United States Patent
Anderson et al.

(10) Patent No.: US 9,403,759 B2
(45) Date of Patent: Aug. 2, 2016

(54) WATER FEED METHODS TO CONTROL MW DISTRIBUTION AND BYPRODUCTS OF THE CARBAMYLATION OF UREA

(71) Applicant: Dow Global Technologies LLC, Midland, MI (US)

(72) Inventors: Jeff R. Anderson, Tomball, TX (US); Daryoosh Beigzadeh, Midland, TX (US); Yiyong He, Midland, TX (US); Congcong Lu, Phoenixville, PA (US)

(73) Assignee: Dow Global Technologies LLC, Midland, MI (US)

(*) Notice: Subject to any disclaimer, the term of this patent is extended or adjusted under 35 U.S.C. 154(b) by 0 days.

(21) Appl. No.: 14/721,423

(22) Filed: May 26, 2015

(65) Prior Publication Data

US 2015/0344417 A1  Dec. 3, 2015

Related U.S. Application Data

(60) Provisional application No. 62/004,545, filed on May 29, 2014.

(51) Int. Cl.
| | | |
|---|---|---|
| *C08G 18/06* | (2006.01) | |
| *C07C 269/04* | (2006.01) | |
| *C08G 71/02* | (2006.01) | |
| *C08G 18/79* | (2006.01) | |
| *C08G 18/38* | (2006.01) | |

(52) U.S. Cl.
CPC .............. *C07C 269/04* (2013.01); *C08G 71/02* (2013.01); *C08G 18/06* (2013.01); *C08G 18/38* (2013.01); *C08G 18/3823* (2013.01); *C08G 18/79* (2013.01)

(58) Field of Classification Search
CPC ........ C08G 18/06; C08G 18/38; C08G 18/79; C08G 71/02; C07C 269/04
USPC ........................................................ 560/158
See application file for complete search history.

(56) References Cited

U.S. PATENT DOCUMENTS

| | | | | |
|---|---|---|---|---|
| 2,956,964 | A * | 10/1960 | Christenson | ........... C08G 12/20 106/169.47 |
| 4,410,697 | A | 10/1983 | Torok et al. | |
| 5,665,433 | A | 9/1997 | Moussa et al. | |
| 5,945,460 | A | 8/1999 | Ekart et al. | |
| 6,541,594 | B2 | 4/2003 | Ohrbom et al. | |
| 8,653,174 | B2 * | 2/2014 | Anderson | ........... C08G 18/3831 524/391 |
| 2005/0147583 | A1 | 7/2005 | Bentley et al. | |
| 2005/0209435 | A1 | 9/2005 | Hirokane et al. | |
| 2007/0252106 | A1 | 11/2007 | Buchold et al. | |

FOREIGN PATENT DOCUMENTS

EP  2397506 A1 * 12/2011 .......... C08G 18/3831

OTHER PUBLICATIONS

V. I. Kucheryavyi et al., "Kinetics of urea hydrolysis at high temperatures applicable to the purification of waste water in urea production," Zhurnal prikladnoi khimii (Leningrad, R.S.F.S.R.), vol. 42, No. 7, 1969; pp. 1596-1600. (Abstract Only).

* cited by examiner

*Primary Examiner* — Kamal Saeed
*Assistant Examiner* — Janet L Coppins
(74) *Attorney, Agent, or Firm* — Andrew Merriam

(57) ABSTRACT

The present invention provides methods for making a polycarbamate by feeding a) a urea in fluid form into a reaction medium containing b) an alkyd polyol, such as a short or med oil alkyd polyol to form a reaction mixture and then carbamylating the alkyd polyol by heating the reaction mixture while feeding water in to the reaction mixture, preferably, in the presence of one or more c) carbamylation catalysts. The polycarbamate of the present invention when combined with a polyaldehyde or an acetal or hemiacetal thereof as a second component makes a multicomponent composition that is substantially isocyanate-free, and cures at a temperature of from 0° C. to less than 80° C. to form a crosslinked polyurethane.

12 Claims, No Drawings

WATER FEED METHODS TO CONTROL MW DISTRIBUTION AND BYPRODUCTS OF THE CARBAMYLATION OF UREA

The present invention relates to methods of making a polycarbamate for use in making polyurethanes comprising feeding a) a urea or alkyl carbamate in fluid form into a reaction medium containing b) an alkyd polyol, preferably, a short or med oil alkyd polyol, to form a reaction mixture and carbamylating the alkyd polyol and then feeding water in to the reaction mixture, preferably, in the presence of one or more transcarbamylation catalysts, such as dibutyl tin oxide.

Polyurethanes find wide use as polymers; they are composed of an organic backbone having repeating units of carbamate linkages. Polyurethanes comprise repeat units that contain carbamate groups of formula (A): —O—C(=O)—N<. Polyurethanes may be made from (poly)isocyanates; however, such (poly)isocyanates and even the residual isocyanates in the polyurethanes have given rise to many health and safety concerns.

Isocyanate free polyurethane compositions have sought to address the health and safety concerns stemming from isocyanates and their residuals. Known isocyanate-free polyurethane must be cured at curing temperatures above 80° C. to achieve effective curing and give a crosslinked polyurethane. The high cure temperature deficiency of prior art isocyanate-free polyurethane preparations prevents them from being used in floor, furniture, automotive, industrial maintenance and adhesive applications requiring curing at ambient temperatures, for example, room temperature (e.g. 20° C. to 30° C.). Further, known isocyanate-free polyurethane compositions can produce unwanted volatile organic compound (VOC) byproducts.

Recently, polyurethanes have been produced from polyols and alkyl carbamates or polycarbamates with co-reactive resins, such as polyaldehydes. Such polyurethanes are substantially isocyanate free. However, such polycarbamates also have proven difficult to make safely and efficiently. For example, known transcarbamylation methods for making polycarbamates from alkyds can be performed using various polyalcohols, including alkyd polyols. However, such transcarbamylation methods result in unwanted resin branching and molecular weight (MW) control issues. In severe cases, the resulting products form micro-gels which are not soluble in solvents and have to be discarded. In addition, residual urea, biuret, cyanuric acid, polyallophanate and phthalimide are byproducts present in the polycarbamate product and are considered impurities. Such impurities can react in use or application and are not desirable.

U.S. Pat. No. 8,653,174 B2, to Anderson et al., discloses multicomponent compositions that are substantially isocyanate-free and comprise a polycarbamate as one component, and a polyaldehyde or an acetal or hemiacetal thereof as a second component such that the two components cure at a temperature of from 0° C. to less than 80° C. to form a crosslinked polyurethane. Anderson discloses transcarbamylation of polyols to make polycarbamates. However, Anderson fails to address the undesirable molecular weight increase or the impurities that result when transcarbamylating an alkyd polyol.

The present inventors have sought to solve the problem of undesirable viscosity buildup or molecular weight (MW) increase and unwanted residual impurities in making polycarbamates from an alkyd polyol.

STATEMENT OF THE INVENTION

1. In accordance with the present invention, methods of making a polycarbamate for use in making polyurethanes feeding one or more a) ureas or alkyl carbamates, such as methyl carbamate, in fluid form into a reaction medium containing one or more b) alkyd polyols, preferably, short or med oil alkyd polyols, to form a reaction mixture and then carbamylating the alkyd polyol by heating the reaction mixture while feeding water in to the reaction mixture, preferably, in the presence of one or more c) carbamylation catalysts, such as dibutyl tin oxide.

2. The methods in accordance with the methods of 1 above, wherein at least one of the b) alkyd polyols has a hydroxyl number of from 50 to 250 hydroxyl groups or, preferably, from 100 to 225.

3. The methods in accordance with the methods of 1 or 2, above, wherein at least one of the b) one or more alkyd polyols is the reaction product of one or more monocarboxylic acid oils, one or more polycarboxylic acids having two or more carboxylic acid, salt or halide groups, or the anhydrides thereof, and one or more polyalcohols having three or more, preferably from three to five, hydroxyl groups, such as erythritol, pentaerythritol, trimethylolpropane, or trimethylolethane.

4. The methods in accordance with the methods of 3, above, wherein the one or more monocarboxylic acid oil used to make the at least one of the b) alkyd polyols is chosen from oleic acid, lauric acid, coconut oil, sunflower oil, and mixtures thereof.

5. The methods in accordance with the methods of 1, 2, 3, or 4, above, wherein the one or more a) ureas or alkyl carbamates is a urea chosen from urea, biuret, triuret, N-substituted $C_1$ to $C_6$ alkyl ureas, such as N-methyl urea or N-ethyl urea, and mixtures thereof.

6. The methods in accordance with the methods of 1, 2, 3, 4 or 5, above, wherein the molar ratio of the total moles of a) ureas or alkyl carbamates to the total number of moles of hydroxyl groups in the one or more b) alkyd polyols in reaction mixture ranges from 0.1:1 to 2.0:1 or, preferably, from 0.4:1 to 1.0:1.

7. The methods in accordance with the methods of any of 1 to 6, above, wherein the one or more a) ureas or alkyl carbamates in fluid form is fed into the reaction medium as a 5 to 80 wt. % solution in water, preferably, from 30 to 50 wt. %.

8. The methods in accordance with the methods of any of 1, 2, 3, 4, 5, 6, or 7, above, wherein the feeding water begins from up to 8 hours, or 0 to 8 hours, after the end of the feeding of the one or more a) ureas or alkyl carbamates to form the reaction mixture, preferably, from 0 to 4 hours after.

9. The methods in accordance with the methods of any of 1, 2, 3, 4, 5, 6, 7, or 8, above, wherein the rate of the feeding water into the reaction mixture ranges from 2 to 20 wt. %/hour, based on the total weight of solids in the reaction mixture or, preferably, from 1.5 to 4 wt. %/hour.

10. The methods in accordance with the methods of any of 1, 2, 3, 4, 5, 6, 7, 8, or 9 above, wherein the carbamylating continues for a total reaction time ranging from 8 to 40 hours, preferably 18 to 30 hours.

11. The methods in accordance with the methods of any of 1 to 10, above, the methods further comprising azeotropically distilling the reaction mixture, preferably, during the carbamylating of the reaction mixture.

12. The methods in accordance with the methods of any of 1 to 11, above, wherein the reaction mixture further comprises c) one or more catalysts.

13. The methods in accordance with the methods of any of 1 to 12, above, wherein the heating the reaction mixture raises the temperature of the reaction mixture to from 100 to 180° C. or, preferably, from 130 to 165° C.

In another aspect, the present invention provides substantially isocyanate-free multicomponent compositions having a pH of 7.0 or less comprising the polycarbamate of the present invention as a first component and one or more polyaldehyde or an acetal or hemiacetal thereof as a second component having two or more aldehyde or an acetal or hemiacetal groups, the multicomponent composition further comprising an effective amount of one or more triggering agent, such as a Lewis acid or acid with a pKa of less than 5.0, such that the first and second components when combined form a composition that reacts to cure at a temperature of from 0° C. to less than 80° C. to form a crosslinked polyurethane.

In the second component of the compositions of the present invention, the one or more polyaldehyde, acetal or hemiacetal thereof may have a solubility in water of less than 0.15 gram of polyaldehyde per milliliter of water at 25° C., and is, preferably, a cycloaliphatic polyaldehyde, such as one chosen from (cis,trans)-1,4-cyclohexanedicarboxyaldehydes, (cis,trans)-1,3-cyclohexanedicarboxyaldehydes and mixtures thereof. Less preferred are more water soluble polyaldehydes, such as glyoxal or glutaraldehyde.

In yet still another aspect, the present invention provides crosslinked polyurethanes prepared by the methods of the present invention.

As used herein, the term "alkyd" means a polyester made from reacting one or more polyalcohols and one or more polycarboxylic acids or their anhydrides, along with one or more monocarboxylic acids, such as long-chain fatty acids, their corresponding triglycerides, and mixtures thereof. The term "oil-based alkyd resin" means a polyester which has been modified by addition of saturated or unsaturated fatty acids or their corresponding triglycerides; and the term "oil-free alkyd resin" means polyesters that have been modified by addition of saturated monocarboxylic acids.

As used herein, the term "drying alkyd resins" means those alkyds made from polyunsaturated fatty acids or triglycerides (drying oils), such as linseed oil, that can dry by air oxidation, or autoxidative drying. Drying alkyds are usually used as the film former of coatings or inks.

As used herein, the term "non-drying alkyd resins" means those alkyds made from non-drying monocarboxylic acid oils, such as coconut oil. Non-drying alkyds may be crosslinked through their hydroxyl functional groups to become part of the film-former.

As used herein, terms referring to "oil lengths" of alkyd resins, e.g., short oil, medium oil or long oil alkyd refer to the proportion of the oil or fatty acid in the alkyd resin, by the weight percent of fatty acids or triglyceride in the alkyd, based on total solids. Alkyd resins are classified, as follows: "Very long" is over 70%, "long" is 56-70%, "medium" is 46-55% and "short" is below 45%.

As used herein, the term "number of moles of hydroxyl groups" of alkyd polyols in a reaction mixture refers to the sum total of the mass of each alkyd polyol used divided by its hydroxyl equivalent weight (OHEW) of the alkyd polyol. The OHEW of any given alkyd polyol equals 56,100 (g/mole KOH) divided by the hydroxyl number of that alkyd polyol in mg alkyd polyol/g KOH. Thus, the number of moles of hydroxyl groups of alkyd polyol in a reaction mixture containing 10 g of each of an alkyd polyol having a hydroxyl number of 100 and an alkyd polyol having a hydroxyl number of 250 equals 10/(56100/100) plus 10/(56100/250) or 10/560 plus 10/224.4 or (0.178+0.446) or 0.624 moles OH.

As used herein, the term "hydroxyl number" or "OH number" of an alkyd polyol is expressed as number of milligrams of potassium hydroxide (KOH) per gram polyol (mg KOH/g alkyd polyol) and means the amount in milligrams of potassium hydroxide (KOH) per gram polyol (mg KOH/g polyol) determined by following the titration methods set forth in ASTM D4274-11 (Standard Test Methods for Testing Polyurethane Raw Materials: Determination of Hydroxyl Numbers of Polyols (2011) Test Method A) performed at room temperature using as reagents 4-(dimethylamino) pyridine catalyst in tetrahydrofuran (THF) and acetic anhydride in THF and as titrant with 1N KOH in methanol.

As used herein, the term "ambient temperature curable" means capable of reacting in a chemically transforming process at from 0° C. to less than 80° C.

As used herein, the term "curing" means subjecting to conditions effective for chemically transforming or chemically transforming under such conditions.

As used herein, the term "curing temperature" means a degree of heat or cold effective for chemically transforming the invention ambient temperature curable composition to the invention crosslinked polyurethane.

As used herein, the term "multicomponent composition" means a composition comprising two or more components, each one having at least one ingredient.

As used herein, the term "polyaldehyde" means a molecule containing two or more aldehyde groups or their hydrates, acetals or hemiacetals, wherein the molecule is capable of performing as described herein and is capable of reacting with the polycarbamate during the invention curing step so as to form the invention crosslinked polyurethane. The aldehyde group can be written herein as —C(=O)H or —CHO. The term "polyaldehyde" is not used herein to mean a polymeric substance made by self-polymerizing an aldehyde monomer.

As used herein, the term "polycarbamate" means a molecule containing two or more carbamate groups ($H_2NC(=O)O-$), wherein the molecule is capable of reacting with a polyaldehyde during curing so as to form a polyurethane.

As used herein, the term "average number of carbamate groups" means the total number average molecular weight of a given polycarbamate as determined by gel permeation chromatography against a polystyrene standard divided by the carbamate equivalent weight of the polycarbamate.

As used herein, the term "carbamate equivalent weight" (CEW) on solids is calculated using the following equation:

$$CEW = (OHEW_{polyol} \div (43 \times \text{Carbamate Conversion})) \div \text{Carbamate Conversion},$$

wherein the term "Carbamate Conversion" is a ratio determined using the following equation:

$$\text{Carbamate Conversion} = (OH\#_{polyol} - OH\#_{polycarbamate}) \div OH\#_{polyol}$$

Note that a Carbamate Conversion can be expressed as a percentage when multiplied by 100%.

As used herein, the term "solvent/diluents" as used herein comprises all conventional non-polar and polar organic solvents and diluents such as, for example, an alkane (e.g., a ($C_6$-$C_{12}$)alkane), ether (e.g., a ($C_2$-$C_{12}$)dialkyl ether), aliphatic esters (e.g., a ($C_2$-$C_{12}$)carboxylic ester), aliphatic ketones (e.g., a ($C_3$-$C_{12}$)ketone), secondary or tertiary carboxamide (e.g., a secondary or tertiary ($C_3$-$C_{12}$)carboxamide), sulfoxide (e.g., a ($C_2$-$C_{12}$)sulfoxide), aliphatic hydrocarbons, aromatic hydrocarbons, mixtures thereof and mixtures thereof with white spirit.

As used herein, the term "substantially free of isocyanate groups" or "substantially isocyanate-free" isocyanate groups means having less than 5 mole percent (mol %) of —N=C=O groups (i.e., isocyanate groups) based on total moles of carbamate groups plus isocyanate groups in the composition, preferably, less than 3 mol %, or, more preferably, less than 1 mol %, and, still more preferably, less than 0.1 mol %.

As used herein, the term "substantially formaldehyde free" is less than 500 ppm based on the weight of polyaldehyde solids.

As used herein, the term "total solids" or "solids" refers to resins, reactants and all non-volatile additives or ingredients, including catalysts; solids does not include water or solvents.

Unless otherwise stated, all units of pressure and temperature refer to standard pressure and room temperature.

Unless otherwise stated, all ranges are inclusive and combinable. For example a stated range of from 0.5 wt. % to 90 wt. %, or, preferably, at most 60 wt. %, and, more preferably, at most 50 wt. %, with preferable minimum amounts of at least 1 wt. %, or, more preferably, at least 2 wt. % will read on ranges of from 0.5 wt. % to 90 wt. %, from 0.5 to 60 wt. %, or, from 0.5 to 50 wt. %, or, from 1 to 90 wt. %, or, preferably, from 1 to 60 wt. %, or, preferably, from 2 to 60 wt. %, or, preferably, from 1 to 50 wt. %, or, more preferably, from 2 to 50 wt. %.

The acronym "ANSI" stands for American National Standards Institute, the name of an organization headquartered in Washington, D.C., USA. The acronym "ASTM" stands for ASTM International, the name of an organization headquartered in West Conshohocken, Pa., USA; ASTM International was previously known as the American Society for Testing and Materials. The acronym "ISO" stands for International Organization for Standardization, the name of an organization headquartered in Geneva 20, Switzerland.

The present invention enables improved control of the production of polycarbamates from alkyd polyols, and reduced contents of undesirable residual chemicals. The feeding of water into the reaction mixture of an alkyd polyol and a urea or alkyl carbamate in any known manner, i.e., at a rate which is constant, or which changes in a linear or non-linear fashion, has been found to hydrolyze residuals, such as urea (if any) and reduce other impurities including biuret and allophanate. In addition, the feeding of water into the reaction mixture of the present invention suppresses undesirable molecular weight build-up in the product polycarbamate formed in the reaction of the present invention. The methods of the present invention provide polycarbamates having a controlled viscosity. Such polycarbamates are useful in making robust polyurethanes, such as crosslinked polyurethanes that provide coatings having resistance to wear and water penetration, as well as sealants, adhesives and manufactured articles, such as foams.

The polycarbamates of the present invention are prepared by reacting the reaction mixture of one or more b) short or med oil alkyd polyol with the one or more a) ureas or alkyl carbamates. The methods comprise feeding the one or more a) ureas or alkyl carbamates in fluid form into a reaction medium comprising one or more b) alkyd polyols in bulk form or dissolved or dispersed in solvent to form a reaction mixture, followed by feeding water into the reaction mixture for a time.

The total feed time for the feeding of the one or more a) ureas or alkyl carbamates in fluid form into a reaction medium comprising the one or more alkyd polyols may range from 1 to 16 hours, for example, 1.5 to 10 hours, and is stopped before or at the time the feeding of water begins.

The methods of the present invention comprise carbamylating one or more b) alkyd polyol in a reaction mixture comprising the b) alkyd polyol and one or more a) ureas or alkyl carbamates in fluid form by heating the reaction mixture while feeding water in to the reaction mixture.

In accordance with the methods of the present invention, the heating of the reaction mixture raises the temperature of the reaction mixture to from 100 to 180° C., or, preferably, from 130 to 165° C. The desired temperature of the reaction mixture depends on solvent used. Lower temperatures are used for solvents that boil (develop a vapor pressure of 1 atmosphere) at temperatures below 100° C. or below 130° C. Higher reaction temperatures help to drive off less volatile solvents, such as aromatic hydrocarbons.

In accordance with the methods of the present invention, the total reaction time of the carbamylating takes place may range from 8 to 40 hours, or, preferably, from 18 to 30 hours.

Preferably, the reaction time used on the methods of the present invention is the shortest possible total reaction time needed to get the highest yield of polycarbamate, based on reactant solids. This is because longer cooking times lead to more branching and more uncontrolled molecular weight increase. The water feeding enables shorter reaction time than in the absence of water feeding.

The reaction may take place in any known suitable reaction vessel or apparatus, which may be, for example, a continuous loop reactor or a kettle equipped with one or more devolatilizers or condensors.

The methods of the present invention preferably further comprise azeotropically distilling the reaction mixture. The azeotrope can be reused as a solvent or carrier depending on the reaction mixture used. Preferably, the azeotrope can be used as a solvent for a reproduction of the carbamylation of the same a) ureas and b) alkyd polyols used in the reaction mixture from which the azeotrope was generated. For example, the distillate may be phase separated in a continuous decanter and the xylene phase returned to the reactor.

The methods can comprise carbamylating while azeotropically distilling the reaction mixture and using a nitrogen or non-condensible gas sparge to facilitate removal of impurities.

Preferably, carbamylation is carried out under at least partial vacuum conditions, thereby creating an internal boiling or stripping action to remove ammonia without using a non-condensable gas. Water in the urea feed is azeotropically distilled with the solvent, e.g., o-xylene, thereby facilitating removal of ammonia in the condensed vapor leaving the reactor.

Azeotropically distilling the reaction mixture could include a very slow gas sparge to facilitate the vacuum stripping action created by the boiling action. For example, an applied vacuum of 400-450 Torr and a very slow nitrogen gas sparging rate (0.3-0.5 sccm) produced a 75% reduction in the level of alkyl carbamate side product compared to the same reaction with nitrogen sparging only (no vacuum) at a higher rate (20 sccm).

More preferably, azeotropically distilling the reaction mixture under vacuum conditions during carbamylation further comprises feeding a slow trickle of water after the urea addition is complete may facilitate more effective ammonia removal. Likewise, a counter-current water spray (contact condenser) may be employed to condense and adsorb ammonia from the distillate phase and to dissolve trace urea present in the reactor.

Compounds suitable as the one or more a) ureas for making the alkyd polyol of the present invention may be any of urea itself, thiourea, biuret, triuret, N-alkyl substituted ureas that have a low level of toxicity, such as N-methyl urea or N-ethyl urea, and urea clathrates. Substituted ureas can be made by conventional methods as disclosed in U.S. Pat. No. 4,410,697A, to Sandor et al. A urea clathrate, also known as a urea inclusion compound, may have a structure as described in "Supramolecular Chemistry" John Wiley & Sons, Jonathan w. Steed, Jerry L. Atwood, pp. 393-398 and Harris, K. D. M., "Fundamental and Applied Aspects of Urea and Thiourea Inclusion Compounds", Supramol. Chem. 2007, 19, 47-53.

The a) urea in fluid form may be a liquid urea obtained in any known manner, such as, for example, by dissolving it or dispersing it in one or more solvents selected from water and organic alcohols. The a) urea may be melted or suspended in a clathrate, such as a paraffin or cycloparaffin and rendered fluid by heating.

Compounds suitable as the one or more a) alkyl carbamates for making the alkyd polyol may be any known alkyl carbamate, such as methyl carbamate.

The a) alkyl carbamates may be in any fluid form, such as a solution or dispersion in solvents or a melt.

A suitable b) alkyd polyol of the present invention may be formed from one or more monocarboxylic acid oils, one or more polycarboxylic acids having two or more carboxylic acid, salt or halide groups, or the anhydrides thereof, and one or more polyalcohols having three or more, preferably from three to five, hydroxyl groups. Suitable monocarboxylic acid oils may comprise any fatty acids/triglycerides, saturated monocarboxylic acids or their mixtures. Such oils may be drying (polyunsaturated) or a non-drying, preferably, non-drying oils.

Examples of suitable monocarboxylic acid oils or their corresponding triglycerides for use in making any alkyd polyol of the present invention may include, for example, abietic acid, benzoic acid, tert-butylbenzoic acid, caproic acid, capric acid, acrylic acid, methacrylic acid, crotonic acid, iso-crotonic acid, 2-ethylhexanoic acid, 2-propylheptanoic acid, $C_{12}$ to $C_{32}$ ethylenically unsaturated fatty acids, such as castor fatty acid or castor oil, coconut fatty acid or coconut oil, cottonseed fatty acid or cottonseed oil, lauric acid, linoleic acid, oleic acid, pelargonic acid, arachidonic acid, elupanodonic acid, soybean fatty acid or soybean oil, tall oil fatty acid, safflower fatty acid or safflower oil, linseed fatty acid or linseed oil, sunflower fatty acid or sunflower oil, linolenic acid, eleostearic acid, tung oil, poppy seed oil, perilla oil, oiticia oil, fish oil, dehydrated castor oil, castor oil fatty acid, almond oil, bassau oil, cocoa butter oil, macadamia oil, olive oil, peanut oil and/or nahar seed oil.

The monocarboxylic acid oils for making the alkyd polyol of the present invention may suitably further comprise at least one hydroxyfunctional carboxylic acid, such as but not limited to dimethylolpropionic acid, dimethylolbutyric acid, trihydroxymethylacetic acid, dihydroxymethylvaleric acid, dihydroxypropionic acid, heptanoic acid, citric acid, tartaric acid, dihydroxymalonic acid, gluconic acid, dihydroxybenzoic acid, hydroxyvaleric acid, hydroxypropionic acid and/or hydroxypivalic acid.

Suitable polycarboxylic acids for making the alkyd polyol of the present invention may be, for example, any one or more aliphatic, cycloaliphatic or aromatic polycarboxylic acids or their corresponding anhydrides, alkyl esters or halides that have two or more carboxyl, carboxylate, or acyl halide groups, such as, for example, o-phthalic acid or anhydride, isophthalic acid, terephthalic acid, trimellitic acid or anhydride, pyromellitic acid or anhydride, 1,2-cyclohexane-dicarboxylic acid or anhydride, 1,3-cyclohexanedicarboxylic acid, 1,4-cyclohexandicarboxylic acid, tetrahydrophthalic acid or anhydride, malic acid, maleic anhydride, fumaric acid, adipic acid, azelaic acid, succinic acid or anhydride, tartaric acid, caproic acid citric acid, sebacic acid, itaconic acid, citraconic acid, their mixtures, and their racemates.

Suitable polyalcohols for making the b) alkyd polyol of the present invention may include, for example, any linear or branched aliphatic, cycloaliphatic or aromatic polyalcohol having three or more hydroxyl groups, or a mixture containing such a polyalcohol with any polyalcohol having two or more hydroxyl groups. Regardless of their number of hydroxyl groups, such polyalcohols may be chosen from polyester polyalcohols, polyether polyalcohols, alkylene glycols, 1,4-butanediol, cyclohexanedimethanols, poly(alkylene) glycols, 2-alkyl-1,3-propanediol or a dimer, trimer or polymer thereof, 2,2-dialkyl-1,3-propanediol or a dimer, trimer or polymer thereof, polycarbonate polyols, glycerol, trimethylolpropane, erythritol, pentaerythritol and dipentaerythritol, sugar alcohols, such as sorbitol, mannitol, and/or any polyalcohol that has been polyalkoxylated, such as a polymethoxylated, polyethoxylated and/or polypropoxylated. The term "alkyl" in this paragraph is herein preferably $C_1$-$C_6$.

To insure that the one or more b) short or med oil alkyd polyol of the present invention has free hydroxyl groups, the short or med oil alkyd is always formed from a reactant mixture that has an excess of total hydroxyl functional groups over total carboxylic, salt, or acyl halide functional groups, preferably, in a ratio of from 3:1 to 1:1, or, more preferably 2.5:1 to 1.5:1

Suitable one or more c) catalysts for carbamylation may comprise, for example, any one or more dibutyltin oxide, dibutyltin acetate; tetravalent metal containing catalysts, such as titanium (IV)-containing compounds and zirconium (IV)-containing compounds, like Ti(IV) isopropoxide, Ti(IV) acetylacetonate, Ti(IV) 2-ethylhexyloxide, tetrabutyl titanate, Ti(IV) butoxy isopropoxy, Ti(IV) oxyacetylacetonate, Ti(IV) bis(acetylacetonate)dichloride, Ti(IV) diisopropoxide bis(acetylacetonate), and chlorotriisopropoxytitanium(IV) Zr (IV) acetylacetonate, Zr(IV) 2-ethylhexanoate, Zr(IV) n-butoxide, Zr(IV) propoxide, Zr(IV) octoate, Zr(IV) tetrakis (trifluoromethanesulfonate), $ZrOCl_2$, $Zr(OH)_4$, and Zr(IV) carboxyethyl acrylate; divalent metal containing catalysts, such as those containing Manganese(II) or Zinc (II), Calcium (II), Magnesium(II), Lead(II), Cobalt (II) and Barium(II), for example, Mn (II) acetylacetonate, Mn(II) 2-ethylhexanoate, Mn(II) bis(trifluoromethanesulfonate), manganese carbonate, $Mn(ClO_4)_2$, manganese halides, manganese(II) hydroxide and manganese (II) oxide; zinc acetylacetonate, Zn (ethylhexanoate)$_2$, Zn(II) triflate, zinc trifluoro acetate hydrate, zinc oxides, zinc halides, zinc hydroxide and zinc halide hydroxide; Ca(II) acetylacetonate, Ca(II) (ethylhexanoate)$_2$, Ca(II) bis(trifluoromethanesulfonate), calcium carbonate, Ca(ClO4)$_2$, calcium halides, calcium hydroxide, calcium methoxide, calcium ethoxide, calcium isopropoxide and Ca(II)oxide; Mg(II) acetylacetonate, Mg(II)(ethylhexanoate)$_2$, Mg(II) bis(trifluoromethanesulfonate), Magnesium carbonate, Mg(ClO4)$_2$, magnesium halides, magnesium hydroxide, magnesium ethoxide, magnesium butoxide, and Mg(II)oxide; Pb(II) acetylacetonate, Pb(II)(ethylhexanoate)$_2$, Pb(II) trifluoromethanesulfonate, Pb(II) hydroxide, lead(II) halides and Pb(II) oxide; Co(II) acetylacetonate, Co(II)(ethylhexanoate)$_2$, Co(II) trifluoromethanesulfonate, cobalt(II) halides, cobalt(II) hydroxide and cobalt(II) oxide; Ba(II) acetylacetonate, Ba(II)(ethylhexanoate)$_2$, Ba(II)bis-(trifluoromethanesulfonate), barium carbonate, $Ba(ClO_4)_2$, barium hydroxide and ba(II)oxide; trivalent metal containing catalysts, such as those containing Bismuth(III) ("Bi(III)"), Aluminum(III) ("Al(III)"), Ytterbium (III) ("Yb(III)"), Yttrium (III) ("Y(III)"), Iron (III) ("Fe(III)"), Lanthanum (III) ("La(III)"), Samarium (III) ("Sm(III)") and Ruthenium(III) ("Ru(III)"), for example, Bismuth (III) acetate, Fe(III) tris(2-ethylhexanoate), Fe(III) oxide, Fe(III) isopropoxide, Fe(III) chloride and Fe(III) bromide. Fe(III)

tris(2-ethylhexanoate), Fe(III) oxide, Fe(III)isopropoxide, Fe(III) chloride and Fe(III) bromide.

The one or more suitable c) catalysts may be used in a total amount of from 0.0001 wt. % to 3 wt. %, or, preferably, from 0.1 wt. % to 0.8 wt. %, based on total reaction mixture solids.

The multicomponent compositions of the present invention comprise the one or more polycarbamate of the present invention and one or more polyaldehydes.

Suitable polyaldehydes for making the multicomponent compositions of the present invention may have two, three, four or more aldehyde groups. A polyaldehyde having three aldehyde groups is referred to herein as a "trialdehyde". The polyaldehyde can be any having from 2 to 100 carbons, with the proviso that polyaldehydes having more than 20 carbon atoms will have at least one aldehyde group for every 11 carbon atoms. The polyaldehyde of the present invention is substantially formaldehyde free.

Suitable polyaldehydes may comprise one or more acyclic, straight or branched polyaldehyde, such as one having from 2 to 16 carbon atoms, or those having 16 carbon atoms prepared by hydroformylating a substantially water insoluble multi-olefin-containing compound that is made from a fatty acid ester or a seed oil, such as a multi-olefin-containing fatty acid triglyceride having 48 carbon atoms or more.

The one or more polyaldehydes of the present invention can be unblocked and unprotected or blocked or protected.

Preferably, the polyaldehydes of the present invention comprises one or more cycloaliphatic polyaldehydes or one or more aromatic polyaldehydes, such as, for example, a cycloaliphatic polyaldehyde having from 3 to 20 ring carbon atoms, or, preferably, from 5 to 12 ring carbon atoms.

The multicomponent compositions, ambient temperature curable compositions, or both of the present invention independently may further comprise one or more additional ingredients. Examples of the additional ingredients are one or more organic solvent, in the total amount of 0.1 weight percent (wt. %) to 90 wt. %, based on the total weight of solids in the compositions; one or more triggering agents; one or more curing inhibitors or polar protic additives, such as water or lower alkanols; one or more dehydrating agent, such as, for example, carboxylic anhydrides, carboxylic acid halides (e.g., acetyl chloride), and sulfonic acid halides (e.g., toluenesulfonyl chloride) in the total amount of 0.01 wt. % to 10 wt. %, based on the total weight of solids in the composition; as well as any of a surfactant, a dispersing agent, a wetting agent, an adhesion promoter, an ultraviolet (UV) light absorber, a light stabilizer, one or more colorants, pigments, extenders or dyes, and antioxidants.

Suitable pigments may include $TiO_2$, lamp black, iron oxides and colored metal oxides, such as copper oxides. Suitable extenders may include, for example, talc, calcium carbonate, and clays.

According to the present invention, ambient temperature curable compositions may consist essentially of a mixture of the one or more polycarbamate of the present invention, the one or more polyaldehyde and a triggering agent. Suitable triggering agents of the present invention may be any compound, substance or material suitable for increasing a rate of reaction of a carbamate group (—O—C(=O)—$NH_2$) with an aldehyde group (—C(=O)H). Examples of triggering agents are Lewis acids (e.g., boron trifluoride etherate) and protic acids (i.e., Brønsted acids).

The triggering agent can be unsupported (no solid support) or supported, i.e., covalently bonded to a solid support. Examples of supported triggering agents are supported curing catalysts such as supported acid catalysts such as acid (H±) forms of cation exchange-type polymer resins (e.g., ethanesulfonic acid, 2-[1-[difluoro[(1,2,2-trifluoroethenyl)oxy]methyl]-1,2,2,2-tetrafluoroethoxy]-1,1,2,2-tetrafluoro-, polymer with 1,1,2,2-tetrafluoroethene sold under trade name NAFION NR 50 (E. I. du Pont de Nemours & Co., Inc., Wilmington, Del.) and ethenylbenzenesulfonic acid polymer with diethenylbenzene sold as AMBERLYST™ 15 (The Dow Chemical Company, Midland, Mich., USA.).

Preferably the triggering agent comprises a protic acid characterizable as having a $pK_a$ of 6 or lower, wherein $pK_a$ is negative base-10 logarithm of acid dissociation constant, $K_a$, of the protic acid. Thus, the ambient temperature curable composition of the present invention has a pH of 7.0, or less, preferably, from pH 3 to pH<6. A preferred protic acid is an inorganic protic acid or organic protic acid. A preferred inorganic protic acid is phosphoric acid or sulfuric acid. A preferred organic protic acid is carboxylic acid, phosphonic acid, or sulfonic acid. A preferred carboxylic acid is acetic acid, trifluoroacetic acid, propionic acid, or a dicarboxylic acid. A preferred phosphonic acid is methylphosphonic acid. A preferred sulfonic acid is methanesulfonic acid, benzenesulfonic acid, a camphorsulfonic acid; para-toluenesulfonic acid, or dodecylbenzenesulfonic acid. Examples of suitable Lewis acid curing catalysts are $AlCl_3$; benzyltriethylammonium chloride (TEBAC);

$Cu(O_3SCF_3)_2$; $(CH_3)_2BrS^+Br^-$; $FeCl_3$ (e.g., $FeCl_3 \cdot 6H_2O$); $HBF_4$;

$BF_3 \cdot O(CH_2CH_3)_2$; $TiCl_4$; $SnCl_4$; $CrCl_2$; $NiCl_2$; and $Pd(OC(O)CH_3)_2$.

The triggering agent may be used in an amount of from 0.001 wt. % to 10 wt. % of the multicomponent composition, based on total solids in the composition, or, preferably from 0.1 wt. % to 5 wt. % thereof, or, more preferably from 0.1 wt. % to 2 wt. % thereof. Such amounts are referred to herein as "effective amounts" of the triggering agent.

Where the polycarbamate of the present invention comprises the reaction product of one or more alkyd polyol made from a drying oil, the compositions comprising the polycarbamate may further comprise a "drier" or "siccative", which is usually a combination of metal salts, as are well-known in the art and commercially available. Examples of suitable driers are metal salts of (cyclo)aliphatic, natural or synthetic acids, such as, for example, linoleic acid, naphthenic acid and 2-ethyl-hexanoic acid. Cobalt, manganese, lead, zirconium, calcium and zinc are suitable drier metals. Mixtures of driers can also be used. In terms of their metal content, the driers are used in a proportion of 0.001 to 3 wt. %, relative to the composition solids content.

Preferably, to reduce or eliminate the correlation between pot life of a composition and coating drying time or coating hardness, or both upon curing thereof, the multicomponent compositions of the present invention comprise a polar protic additive which acts as a curing inhibitor. The polar protic additive may include, for example, water or alkanols (e.g., ($C_1$-$C_{12}$)alkanols) in the amount of 0.01 wt. % to 90 wt. %, all amounts based on the total weight of solids in the multicomponent compositions, such as from 0.5 wt. % to 90 wt. %, or, preferably, at most 60 wt. %, and, more preferably, at most 50 wt. %. Preferably, minimum amounts are at least 1 wt. %, based on the total weight of solids in the composition, and, still more preferably, at least 2 wt. %.

The multicomponent compositions of the present invention may be used anywhere a crosslinked polyurethane is useful, such as, for example, coatings, sealants, adhesives, articles comprising cast parts (e.g., automobile bumpers), foams, and elastomeric fibers. Coating compositions may include, for example, decorative paints for interior and exterior use, flat house paints, clear or translucent wood finishes, such as floor coatings, and varnishes, automotive coatings, and baking enamels for appliances. Adhesives may include, for example, floor, furniture, automotive, industrial maintenance and certain adhesive applications requiring curing at ambient temperatures. The compositions of the present invention may be useful for preparing articles, such as foams.

The coating compositions of the present invention may further comprise, for example, driers and, if appropriate, solvents/diluents, pigments, dyes, fillers and auxiliaries. Advantageously, the coating compositions of the present invention may have a solids content within the range of from 20 to 90% by volume, preferably 25 to 60% by volume.

The pigment volume concentration (% PVC) of coating compositions comprising multicomponent compositions of the present invention should be adapted to the end use of the compositions, as known in the art; for example, varnishes have a PVC of zero, high gloss paints generally of up to about 20, maintenance paints generally of from 10 to 30, and primers generally of from 20 to 60.

Preferably, methods of using the multicomponent compositions of the present invention comprise applying the compositions to at least a portion of the surface of the substrate and curing the curable coating of the ambient temperature curable composition of the composite material at a curing temperature of 80° C. or less, or, for example, 30° C. or less, so as to prepare a coated substrate comprising a crosslinked polyurethane.

The ambient temperature curable composition of the present invention can be applied to the surface of the substrate(s) by any suitable applying means such as, for example, brushing, calendaring, rolling, spraying, mopping, troweling, or dipping. The substrate being coated, adhered to, or sealed can be of any shape including, for example, a flat or rolled sheet (e.g., cylinder), sphere, beads, finely divided particles, and the like. The surface of the substrate being coated, adhered to, or sealed can be irregular or regular, continuous or discontinuous, porous or non-porous, jointed or not jointed.

The substrates suitable for being adhered to, coated, or sealed independently can comprise any material. Examples of suitable material are wood, lignocellulosic and woody substrates such as wood, plywood, laminates made from wood, bamboo and bamboo laminates, composite board; metals, such as bare metal or metal that has been pretreated or primed, for example to impart corrosion resistance; ceramic, plastic, gypsum board or sheetrock; and glass. Exemplary metal substrates may include, for example, steel, aluminum, copper, zinc, magnesium, and alloys thereof. The components of the compositions can be varied to suit the temperature tolerance of the substrate material.

Preferably, coatings of the present invention exhibit resistance to organic solvent, i.e., methyl ethyl ketone (MEK) back-and-forth double rubbing (i.e., one rub back, one rub forth equals one double rub) of 30 or greater, more preferably, 50 or greater, still more preferably, 70 or greater, even more 100 or greater, and yet more preferably, greater than 200 (>200).

EXAMPLES

The following examples illustrate the present invention:

Example 1-1

Alkyd Polyol I Synthesis

Alkyd polyol I was synthesized by reacting the materials shown in the Table 1-1, below. A round bottom glass reactor, equipped with temperature control, agitation, nitrogen sparger, and short distillation path was used to carry out the synthesis. Isophthalic acid, pentaerythritol, trimethylolethane, oleic acid, and lauric acid were charged as reactants into reactor at room temperature, followed by dibutyl tin oxide and monobutyl tin oxide as catalysts. The reactor content was heated to 220° C. using a mantle heater under nitrogen sparging. Water was generated as a byproduct and was removed from the reactor to drive the reaction forward. Samples were periodically taken to determine the acid value. When acid value approached 6, cooling was started to stop the reaction. The reaction product was discharged when cooled below 140° C. The resulting alkyd polyol had a hydroxyl number of approximately 200.

TABLE 1-1

| Raw Materials (Alkyd polyol I) | Loading (g) |
| --- | --- |
| Isophthalic acid | 339.6 |
| Pentaerythritol | 188.6 |
| Trimethylolethane | 134.7 |
| Oleic acid | 168.4 |
| Lauric acid | 168.4 |
| Dibutyl tin oxide | 0.75 |
| Monobutyl tin oxide | 0.75 |
| Total Batch Size | 1001.5 |

Example 1-2

Alkyd Polyol II Synthesis

Alkyd polyol II was synthesized by reacting the materials shown in Table 1-2, below. A round bottom glass reactor, equipped with temperature control, agitation, nitrogen sparger, and short distillation path was used to carry out the synthesis. This was a two-step synthesis, with first step being alcoholysis and the second being fusion reaction. First, the coconut oil and pentaerythritol were charged into the reactor with dibutyl tin oxide and monobutyl tin oxide as catalysts. The reactor content was heated to 220° C. using a mantle heater under nitrogen sparging, and was held at temperature for 4-6 hr. A methanol test was conducted at the end of the alcoholysis step to confirm that coconut oil was converted into its corresponding fatty acids. The reactor was cooled down to 150° C., followed by addition of isophthalic acid and phthalic anhydride. The reactor content was heated to 220° C. to carry out fusion reaction. Water was produced as a byproduct and removed from the reactor to drive reaction forward. Samples were periodically taken to determine the acid value. When the acid value approached 10, cooling was started to stop the reaction. The resulting alkyd polyol had hydroxyl number of approximately 200.

TABLE 1-2

| Raw Materials (Alkyd Polyol II) | Loading (g) |
| --- | --- |
| Isophthalic acid | 403.8 |
| Pentaerythritol | 480.0 |
| Phthalic anhydride | 214.0 |
| Coconut Oil | 724.8 |
| Dibutyl tin oxide | 1.8 |
| Monobutyl tin oxide | 1.8 |
| Total Batch Size | 1826.2 |

Comparative Example 1

Carbamylation of Alkyd Polyol I

To make the polycarbamate from the reaction mixture shown in the following Table, the reaction mixture was heated to a temperature of 140° C. and reacted for a total reaction time of 21 hours, with the urea solution being fed in into the reactor containing alkyd polyol, catalyst and xylenes at a fixed flow rate over 6 hr. No water feed was used.

| | |
|---|---|
| Alkyd polyol I | 201.6 g |
| Xylene | 75.3 g |
| Urea solution in water (50 wt. %) | 46.1 g |
| Dibutyl tin oxide | 1.8 g |

Comparative Example 2

Carbamylation of Alkyd Polyol I

To make the polycarbamate from the reaction mixture shown in the following Table, the reaction mixture was heated to a temperature of 140° C. and reacted for a total reaction time of 23.5 hours with the urea solution being fed in into the reactor containing alkyd polyol, catalyst and xylenes at a fixed flow rate over 6 hr. No water feed was used.

| | |
|---|---|
| Alkyd polyol I | 459.8 g |
| Xylene | 186.9 g |
| Urea solution in water (45 wt. %) | 118.4 g |
| Dibutyl tin oxide | 1.4 g |

Example 3

Water Feed During Carbamylation of Alkyd Polyol I

To make the polycarbamate from the reaction mixture shown in the following Table, the reaction mixture was heated to a temperature of 140° C. and reacted for a total reaction time of 25.5 hours, with the urea solution being fed in into the reactor containing alkyd polyol, catalyst and xylenes at a fixed flow rate over 6 hr. A water feed was started at 8 hours after the urea feed was started at a controlled feed rate of 10 ml/hour.

| | |
|---|---|
| Alkyd polyol I | 394.2 g |
| Xylene | 160.2 g |
| Urea solution in water (45 wt. %) | 104.4 g |
| Dibutyl tin oxide | 1.2 g |
| Water feed initiated @ | 8 hr |
| Water feed rate | 10 ml/hr |

Comparative Example 4

Carbamylation of Alkyd Polyol II

To make the polycarbamate from the reaction mixture shown in the following Table, the reaction mixture was heated to a temperature of 140° C. and reacted for a total reaction time of 17 hours, with the urea solution being fed in into the reactor containing alkyd polyol, catalyst and xylenes at a fixed flow rate over 6 hr. No water feed was used.

| | |
|---|---|
| Alkyd polyol II | 326.0 g |
| Xylene | 122.9 g |
| Urea solution in water (45 wt. %) | 135.6 g |
| Dibutyl tin oxide | 3.06 g |

Example 5

Water Feed During Carbamylation of Alkyd Polyol II

To make the polycarbamate from the reaction mixture shown in the following Table, the reaction mixture was heated to a temperature of 140° C. and reacted for a total reaction time of 17 hours, with the urea solution being fed in into the reactor containing alkyd polyol, catalyst and xylenes at a fixed flow rate over 6 hr. A water feed was started at 11 hours after the urea feed was started at a controlled feed rate of 10 ml/hour.

| | |
|---|---|
| Alkyd polyol II | 447.5 g |
| Xylene | 168.7 g |
| Urea solution in water (45 wt. %) | 186.2 g |
| Dibutyl tin oxide | 4.2 g |
| Water feed initiated @ | 11 hr |
| Water feed rate | 10 ml/hr |

Test Methods:

The following test methods were used to analyze the polycarbamates of Examples 1 to 5 and to test their performance.

$^{13}$C NMR:

Reaction mixtures were sampled from the reactor at the reaction times indicated in Tables 4 and 5, below, and characterized by $^{13}$C NMR. For each of the reaction mixture samples, 0.8 g reaction mixture was dissolved in 2.4 mL perdeuterated ($d_6$) dimethyl sulfoxide (DMSO-$d_6$) in a glass vial at room temperature. To this vial, 0.015 M chromium (III) acetoacetate Cr(Acac)$_3$ was added as a relaxation agent to shorten data acquisition time. The solution was then transferred to a 10 mm NMR tube. Quantitative inverse-gated $^{13}$C NMR experiments were performed on a Bruker Avance™ 400 MHz (1H frequency) NMR spectrometer (Bruker Corporation, Midland, Mich.) equipped with a 10 mm DUAL C/H cryoprobe. All experiments were carried out at room temperature without sample spinning. A calibrated 90° pulse was applied in the inverse-gated pulse sequence. The relaxation delay between consecutive data acquisitions is 5*$T_1$, where $T_1$ is the longest spin-lattice relaxation time of all nuclei in the measured system. The $^{13}$C NMR spectra were processed with a line broadening of 1 Hz, and referenced to 39.5 ppm for the DMSO-$d_6$ resonance peak.

GPC:

Molecular weight, both weight average($M_W$) and number average ($M_N$) and polydispersity (PDI) values were measured by gel permeation chromatography (GPC) on an Agilent 1260 Infinity series LC system, Santa Clara, Calif. equipped with an Agilent 1260 Infinity series refractive index detector. Samples the indicated polycarbamate were dissolved in HPCL grade THF at a concentration of approximately 10 mg/mL and filtered through at 0.45 μm syringe filter before injection through the two PLGel 300×7.5 mm Mixed B columns (5 mm, Agilent Technologies Inc.). A flow rate of 1 mL/min and temperature of 35° C. were maintained. The columns were calibrated with narrow molecular weight polystyrene (PS) standards (Polystyrene High EasiVials™, Agilent Technologies, Santa Clara, Calif.).

Viscosity:

Viscosity was measured using a TA Instruments AR-2000 rheometer, (TA Instruments, New Castle, Del.). All samples were adjusted to equivalent percent solids of 63% by weight to using xylene to remove the influence of solids on viscosity.

Thickness of the Coating:

ASTM D7091-05 (Standard Practice for Nondestructive Measurement of Dry Film Thickness of Nonmagnetic Coatings Applied to Ferrous Metals and Nonmagnetic, Nonconductive Coatings Applied to Non-Ferrous Metals (2005)).

As shown in Table 2, below, without using water-feed, the weight average molecular weight ($M_W$) of the polymer gradually built up over the course of carbamylation reaction using alkyd polyol I. In comparative Example 2, $M_W$ was increased from 45,000 to 133,300. Number average molecular weight ($M_N$) of the comparative polycarbamate polymers remained almost unchanged, while the molecular weight polydispersity Index (PDI) was significantly increased from 17.3 to 41.0. This indicates crosslinking reaction via branching, which is an undesired side reaction as it alters the polymer structure and leads to high viscosity, which further results in formulation difficulties.

TABLE 2

Molecular weight distribution of Examples 1 and 2

| | Reaction Time (hr) | Mn | Mw | Polydispersity Index |
|---|---|---|---|---|
| Comparative Example 1 | t = 0 hr | 2500 | 47,700 | 18.8 |
| | t = 21 hr | 2700 | 87,500 | 32.5 |
| Comparative Example 2 | t = 0 hr | 2600 | 45,000 | 17.3 |
| | t = 6 hr | 2700 | 34,500 | 12.6 |
| | t = 21.5 hr | 3000 | 93,400 | 31.0 |
| | t = 23.5 hr | 3200 | 133,300 | 41.0 |

As shown in Table 3, below, including a water-feed in the carbamylation reaction using alkyd polyol I greatly suppressed unwanted branching side reaction, resulting in much less Mw buildup. Even after 25 hr of reaction, the Mw only showed a slight increase, to 59,200. This helps to keep the polydispersity index before and after carbamylation relatively constant, an important parameter in evaluating polymer properties.

TABLE 3

Molecular weight distribution of Inventive Example 3.

| Example 3 | Mn | Mw | PDI |
|---|---|---|---|
| t = 0 hr | 2600 | 44,000 | 17.2 |
| t = 11 hr | 2500 | 38,900 | 15.9 |
| t = 18.5 hr | 2400 | 48,600 | 20.1 |
| t = 25.2 hr | 2600 | 59,200 | 22.3 |

Residual urea is present in a final polycarbamate product after a carbamylation reaction and is considered to be an impurity. As shown in Table 4, below, without using a water-feed, the residual urea level in the final product was 0.08% on dry solids basis after ~22 hr of reaction (Examples 1 and 2). The desired product is a polycarbamate, each carbamate group resulting from the hydroxyl functionality on the alkyd polyol through the carbamylation reaction. As shown by Examples 1 and 2, the carbamate conversion % was between 47.4 to 50.1%. In contrast, when using a water-feed during the carbamylation reaction, the residual urea level was reduced to 0.12% at 11 hr., and then further reduced to 0.02% at 14 hr. (Example 3). Accordingly, the water-feed process reduces cycle time significantly, and also reduces the level of impurity (urea). In addition, the water-feed did not have any negative impact on the polycarbamate conversion rate.

TABLE 4

Residual urea and carbamate conversion % of Examples 1, 2 and 3 at Given Reaction Times

| | Residual urea (wt. % on dry solids) | Polycarbamate conversion (mol %) | Reaction time (hr) |
|---|---|---|---|
| *Example 1 | 0.08 | 50.1 | 21 |
| *Example 2 | 0.08 | 47.4 | 21.5 |
| Example 3 | 0.12 (11 hr) | 55.5 | 11 |
| | 0.02 (14 hr) | 52.7 | 14 |

*denotes Comparative Example

In a polycarbamate product from the carbamylation reaction, there are several impurities, such as poly-allophanate, biuret, cyanuric acid and phthalimide. Table 5, below, shows the levels of these impurities in the polycarbamate product. In addition to reducing residual urea, it is evident that water-feed is also effective in suppressing the formation of some impurities, including biuret and poly-allophanate. When water-feed was used, biuret formation was significantly reduced from 0.57% to 0.24% as the reaction continued. Poly-allophanate formation was controlled at 1.1% by water-feed, while it continued to increase to 1.5% when water-feed was not used. In Examples 4 and 5, water-feed also demonstrated positive effect on improving the polycarbamate conversion rate. No adverse effect was observed on the residual content of cyanuric acid and phthalimide from a water-feed process.

TABLE 5

Impurities in the Polycarbamate product

| Ex | Reaction Time (hr) | Polycarbamate (mol %) | Poly-allophanate (mol %) | Biuret | Wt. % on dry solids | | |
|---|---|---|---|---|---|---|---|
| | | | | | Cyanuric acid | Residual Urea | Phthalimide |
| * | 11 | 62.8% | 0.9 | 0.48% | 0.01% | 3.64% | 1.02% |
| Example 4 | 13 | 65.7% | 1.2 | 0.56% | 0.02% | 2.89% | 1.03% |
| | 15 | 66.9% | 1.5 | 0.57% | 0.02% | 2.20% | 1.09% |
| | 17 | 68.1% | 1.5 | 0.53% | 0.03% | 1.79% | 1.05% |
| Example 5 | 11 | 60.9% | 0.8 | 0.57% | 0.01% | 3.95% | 1.00% |
| | 13 | 65.6% | 1.2 | 0.44% | 0.01% | 2.62% | 1.02% |
| | 15 | 69.3% | 1.1 | 0.27% | 0.02% | 1.68% | 1.04% |
| | 17 | 73.0% | 1.1 | 0.24% | 0.03% | 1.15% | 1.05% |

* denotes Comparative Example

Table 6, below, shows the results of the general trend to significantly higher viscosity at higher weight average molecular weights for the polycarbamate of Example 4. The Table demonstrates the desirability of keeping $M_W$ low.

TABLE 6

Viscosity of alkyd polycarbamate by molecular weight

| $M_W$ | Viscosity (Cps) |
|---|---|
| 3800 | 200 |
| 3800 | 300 |
| 26000 | 17800 |
| 42000 | 12800 |

As shown in Table 7, below, the alkyd polyol polycarbamate of Comparative Example 4 was coated on white ceramic tile at a wet film thickness of 127 microns. The coated tiles were allowed to cure under ambient conditions for one hour and then were exposed to 60° C. continuous temperature for 24 hours. Color was measured before and after exposure to elevated temperatures with the resultant difference reported here as ΔE, where small values indicate little or no change and large values (>1.0) indicate noticeable color change. The trend shows that residual urea correlates to higher thermal color instability and is undesirable. Thus, because the present invention provides resins having lowered residual urea contents, the present invention provides resins having improved color stability.

TABLE 7

Color Instability as a Function of Residual Urea Concentration

| Residual urea (wt. %) | ΔE |
|---|---|
| 0.08 | 5.2 |
| 1.37 | 24.3 |
| 3.07 | 38.5 |

We claim:

1. A method of making a polycarbamate for use in making polyurethanes feeding one or more a) ureas or alkyl carbamates in fluid form into a reaction medium containing one or more b) alkyd polyols to form a reaction mixture and then carbamylating the alkyd polyol by heating the reaction mixture while feeding water into the reaction mixture.

2. The method as claimed in claim 1, wherein at least one of the b) alkyd polyols has a hydroxyl number of from 50 to 250.

3. The method as claimed in claim 1, wherein at least one of the b) alkyd polyols is a short or med oil alkyd polyol.

4. The method as claimed in claim 1, wherein at least one of the b) one or more alkyd polyols is the reaction product of one or more monocarboxylic acid oils, one or more polycarboxylic acids having two or more carboxylic acid, salt or acyl halide groups or the anhydride thereof, and one or more polyalcohols having three or more hydroxyl groups.

5. The method as claimed in claim 4, wherein the one or more monocarboxylic acid oil used to make the at least one of the b) alkyd polyols is chosen from oleic acid, lauric acid, coconut oil, sunflower oil, and mixtures thereof.

6. The method as claimed in claim 1, wherein the one or more a) ureas or alkyl carbamates is a urea chosen from urea, biuret, triuret, N-substituted $C_1$ to $C_6$ alkyl ureas, and mixtures thereof.

7. The method as claimed in claim 1, wherein the molar ratio of the total moles of a) ureas or alkyl carbamates to the total number of moles of hydroxyl groups in the one or more b) alkyd polyols in reaction mixture ranges from 0.1:1 to 2.0:1.

8. The method as claimed in claim 1, wherein the one or more a) ureas or alkyl carbamates in fluid form is fed into the reaction medium as a 5 to 80 wt. % solution in water.

9. The method as claimed in claim 1, wherein the feeding of water begins from 0 to 8 hours, after the end of the feeding of the one or more a) ureas or alkyl carbamates into the reaction medium to form the reaction mixture.

10. The method as claimed in claim 1, wherein the rate of the feeding water into the reaction mixture ranges from 2 to 20 wt. %/hour, based on the total weight of solids in the reaction mixture.

11. The method as claimed in claim 1, wherein the carbamylating continues for a total reaction time ranging from 8 to 40 hours.

12. The method as claimed in claim 1, wherein the reaction mixture further comprises one or more c) carbamylation catalysts.

* * * * *